United States Patent [19]
Chiang et al.

[11] Patent Number: 5,994,410
[45] Date of Patent: *Nov. 30, 1999

[54] THERAPEUTIC USE OF WATER-SOLUBLE FULLERENE DERIVATIVES

[75] Inventors: Long Y. Chiang; Yih-Loong Lai; Ming-Cheng Tsai; Yuan-Teh Lee; Huei-Chen Huang; Ming-Kuen Lai; Fong-Jou Lu, all of Taipei, Taiwan

[73] Assignee: National Science Council, Taipei, Taiwan

[*] Notice: This patent is subject to a terminal disclaimer.

[21] Appl. No.: 08/893,299

[22] Filed: Jul. 15, 1997

Related U.S. Application Data

[63] Continuation-in-part of application No. 08/547,714, Oct. 26, 1995, Pat. No. 5,648,523.

[51] Int. Cl.$^6$ ............... A01N 41/10; A01N 31/00; A61K 31/10; A61K 31/045
[52] U.S. Cl. ............... 514/709; 514/710; 514/711; 514/729; 514/731; 514/732; 514/733; 514/734; 514/736; 514/738
[58] Field of Search ............... 518/709, 710, 518/711, 729, 731, 732, 733, 734, 736, 738

[56] References Cited

U.S. PATENT DOCUMENTS

| | | | |
|---|---|---|---|
| 5,177,248 | 1/1993 | Chiang et al. | 560/86 |
| 5,294,732 | 3/1994 | Chiang et al. | 560/86 |
| 5,416,188 | 5/1995 | Chiang et al. | 528/291 |

FOREIGN PATENT DOCUMENTS

| | | |
|---|---|---|
| 0 653 424 A1 | 5/1995 | European Pat. Off. . |
| WO 95/19949 | 7/1995 | WIPO . |

OTHER PUBLICATIONS

Belik et al., "Reaction of Buckminsterfullerene with orth–Quinodimethane: a New Access to Stable $C_{60}$ Derivatives", Angew. Chem. Int. Ed. Engl. 1:78–80, 1993.
Chiang et al., "Efficient Synthesis of Polyhydroxylated Fullerene Derivatives via Hydrolysis of Polycyclosulfated Precursors", J. Org. Chem., 59:3960–3968, 1994.
Chiang et al., "Evidence of Hemiketals Incorporated in the Structure of Fullerols Derived from Aqueous Acid Chemistry", J. Am. Chem. Soc., 115:5453–5457, 1993.
Chiang et al., "Free Radical Scavenging Activity of Water–soluble Fullernols", J. Chem. Soc. Chem. Commun., 1283–1284, 1995.
Chiang et al., "Multi–hydroxy Additions onto $C_{60}$ Fullerene Molecules", J. Chem. Soc. Chem. Commun., 1791–1793, 1992.
Chiang et al., "Versatile Nitronium Chemistry for $C_{60}$ Fullerene Functionalization", J. Am. Chem. Soc., 114:10154–10157, 1992.
Friedman et al., "Inhibition of the HIV–1 Protease by Fullerene Derivatives: Model Building Studies and Experimental Verification", J. Am. Chem. Soc, 115:6506–6509, 1993.
Hirsch et al., "Globe–trotting Hydrogens on the Surface of the Fullerene Compound $C_{60}H_6(N(CH_2CH_2)_2O)_6$", Angew. Chem. Int. Ed. Engl. 30:1309–1310, 1991.
Hoke et al., "Reaction of Fullerenes and Benzyne", J. Org. Chem. 57:5069–5071, 1992.
Isaacs et al., "Improved Purification of $C_{60}$ and Formation of γ and πHomoaromatic Methano–Bridged Fullerenes by Reaction with Alkyl Diazoacetates", Helvetica Chimica Acta 76:1231–1250, 1993.
Juha et al., "Reactivity of Fullerenes with Chemically Generated Singlet Oxygen", J. Chem. Soc., Chem. Commun., 2437–2438, 1994.
Krusic et al., "Radical Reactions of $C_{60}$", Science 254:1183–1185, 1991.
Li et al., "$C_{60}$ Fullerol Formation Catlysed by Quaternary Ammonium Hydroxides", J. Chem. Soc., Chem. Commun. 1784–1785, 1993.
Paulus et al., "Diethyl Methano–$C_{60}$–fullerene–61,61–dicarboxylate Chloroform Solvate at 193K, $C_{60}C(CO_2C_2H_5)_2CHCl_3$", Acta Cryst, C51:143–146, 1995.
Prato et al., "[3+2] and [4+2] Cycloadditions of $C_{60}$", J. Am. Chem. Soc. 115:1594–1595, 1993.
Shu et al., "Reaction of [80]Fullerene with 1–(4–Methoxyphenyl)–1–(trimethylsilyloxy)ethylene", J. Chem. Commun. 367–368, 1995.
Roy et al., "$NO_2$ Adducts of $C_{60}$: Synthesis of Polynitro–Polyhydroxy Fullerenes", J. Chem. Soc., Chem. Commun., 275–276, 1994.
Schneider et al., "Formation of Fullerols via Hydroboration of Fullerene–$C_{60}$", J. Chem. Soc., Chem. Commun., 463–464, 1994.
Suzuki et al., "Systematic Inflation of Buckminsterfullerene $C_{60}$: Synthesis of Diphenyl Fulleriods $C_{61}$ to $C_{66}$", Science 254:1186–1188, 1991.
Taliani et al., "Light–induced Oxygen Incision of $C_{60}$", J. Chem. Soc. Chem. Commun., 220–222, 1993.
Tokuyama et al., "Photoinduced Biochemical Activity of Fullerene Carboxylic Acid", J. Am. Chem. Soc. 115:7918–7919, 1993.
Tsuda et al, "Addition Reaction of Benzyne to $C_{60}$", Chemistry Letters 2333–2334, 1992.
Wilson et al., "A New Reaction of Fullerenes: [2+2] Photocycloaddition of Enones", J. Am. Chem. Soc. 115:8495–8496, 1993.

(List continued on next page.)

Primary Examiner—Frederick Krass
Attorney, Agent, or Firm—Fish & Richardson P.C.

[57] ABSTRACT

A method of treating a free radical-related medical condition. The method includes the step of administering to a subject in need of such treatment an effective amount of a compound of the formula $$F(\text{---}X)_m$$

wherein
F is a fullerene core; each X is independently OH, $(CH_2)_n\text{---}SO_3H$, or a metal salt of $(CH_2)_n\text{---}SO_3^-$ in which each n is independently 2–50; and m is 2–40.

15 Claims, No Drawings

OTHER PUBLICATIONS

Balch et al., "Supramolecular Aggregation of an ($\pi^2$–$C_{60}$) Iridium Complex Involving Phenyl Chelation of the Fullerene", J. Am. Chem. Soc. 114:5455–5457, 1992.

Chiang et al., "Pharmacology", Chemical Abstracts vol. 122, No. 23, Jun. 5, 1995, Abstract No. 281924.

Chiang et al., "Pharmacology", Chemical Abstracts vol. 124, No. 9, Feb. 26, 1996, Abstract No. 106531.

Chiang, et al., "Free–Radical Scavenging Effect of Water–Soluble [60] Fullerenols in Whole Blood . . . ",Proc. Electrochem. Soc. 95–10, 699 (1995).

Huang et al., "Antiproliferative Effect of Polyhydroxylated $C_{60}$ on Vascular Smooth Muscle Cells", Proc.Electrochem. Soc. 96–10, 403 (1996).

THERAPEUTIC USE OF WATER-SOLUBLE FULLERENE DERIVATIVES

CROSS REFERENCE TO RELATED APPLICATIONS

This application is a continuation-in-part of U.S. patent application Ser. No. 08/547,714, filed Oct. 26, 1995, now U.S. Pat. No. 5,648,523.

BACKGROUND OF THE INVENTION

Conjugated caged olefins, such as $C_{60}$ and analogous molecules thereof, have been found to be extraordinarily susceptible to the attack of a variety of chemical reagents. Particularly, they all exhibit high reactivity toward multiple additions of organic free radicals. This reactivity is, presumably, correlated to the intrinsically large electronegativity of such molecules.

Several functionalized fullerene derivatives have been reported for the biochemical or medical related studies. For example, bis(phenethylamino-succinate) $C_{60}$ inhibited the HIV-1 protease. Friedman, et al., J. Am. Chem. Soc. 1993, 115, 6506. As another example, photoactivated water-compatible monofunctionalized $C_{60}$ showed DNA-cleaving activity and in vitro cytotoxicity against the HeLa S3 cell line. Tokuyama, et al., J. Am. Chem. Soc. 1993, 115, 7918. Both activities were eliminated in the absence of a light source.

SUMMARY OF THE INVENTION

An aspect of this invention relates to a pharmaceutical composition for treating a free radical-related medical condition. The composition includes an effective amount of a polyhydroxylated fullerene compound, a poly(sulfonylalkylated) fullerene compound or its metal salt, or a mixed-functional fullerene compound (i.e., containing both hydroxyl and sulfonylalkyl groups) or its metal salt.

More specifically, the compound is of the formula

$$F(-X)_m$$

wherein

F is a fullerene core (e.g., a $C_{60}$ fullerene core); each X is independently OH, $(CH_2)_n$—$SO_3H$, or a metal salt of $(CH_2)_n$—$SO_3^-$ in which each n is independently 2–50; and m is 2–40; and a pharmaceutically acceptable carrier of the compound.

When X in the compound is OH, it is preferred that m be 4–30 or more preferred that m be 10–20. On the other hand, when X in the compound is $(CH_2)_n$—$SO_3H$ or a metal salt of $(CH_2)_n$—$SO_3^-$, it is preferred that m be 2–10 and n be 2–10.

When X is a metal salt of $(CH_2)_n$—$SO_3^-$, the metal can be monovalent (e.g., Na or K) or bivalent (e.g., Ca or Mg).

What is meant by "fullerene core" is a caged molecule consisting essentially of carbon atoms such as $C_{60}$, $C_{60}H_x$, $C_{61}$, $C_{62}$, $C_{71}$, $C_{72}$, $C_{60}O_x$, $C_{60}N_x$, $C_{61}O_x$, $C_{62}O_x$, $C_{70}O_x$, $C_{70}O_x$, $C_{72}O_x$, $C_{70}N_x$, $C_{76}$, $C_{76}O_x$, $C_{78}$, $C_{78}O_x$, $C_{82}$, $C_{82}O_x$, $C_{84}$, $C_{84}O_x$, $C_{92}$, $C_{92}O_x$, and the like, in which x is 1–20 (e.g., 1–8). $C_{60}O_x(OH)_y$ is an example of a fullerene derivative in which $C_{60}O_x$ is the fullerene core with hydroxyl groups linked to it. $C_{60}H_x(NRR')_x$, on the other hand, is an example where $C_{60}H_x$ is the fullerene cage. Of note, the term "$C_{60}$ fullerene core" refers specifically to $C_{60}$, $C_{60}H_x$, $C_{61}$, $C_{62}$, $C_{60}O_x$, $C_{60}N_x$, $C_{61}O_x$, or $C_{62}O_x$.

Another aspect of this invention relates to a method of treating a free radical-related medical condition. The method includes the step of administering to a subject in need of such treatment an effective amount of one or more than one of the above-described compounds.

In addition to the above-described pharmaceutical composition for use as a free radical-scavenging agent, also within the scope of the present invention is the use of such a composition for the manufacture of a medicament for the treatment of a free radical-related medical condition.

Other features or advantages of the present invention will be apparent from the following detailed description of several embodiments, and also from the appending claims.

DETAILED DESCRIPTION OF THE INVENTION

A pharmaceutical composition of this invention can be used to treat a free radical-related medical condition. For example, it can be used as an antioxidant against exsanguination-induced noncholinergic airway constriction, as an inhibitor against peroxide-induced damages on brain tissues, as an inhibitor against lipid and lipoprotein peroxidation, as an antiproliferative agent against the proliferation of T-lymphoid leukemia cells and smooth muscle cells, as an ingredient of the perfusion solution for improving the function of the canine renal grafts, and as a free radical scavenger for preserving ischemia-reperfusion related injuries and for reducing reactive free radicals in the whole blood of patients with cancer. In other words, free radical-related medical conditions include, but are not limited to, ischemia-induced bronchoconstriction, ischemia-reperfusion related injury, cancer, atherosclerosis, and restenosis. Indeed, free radicals are also involved in neurological conditions, such as epilepsy and Parkinson's disease, and therefore the above-described water-soluble fullerene compounds can be used to treat such conditions as well.

Methods of preparing water-soluble polyhydroxylated fullerene derivatives, e.g., $C_{60}(OH)_x$ or $C_{60}O_x(OH)_y$, are well known in the prior art.

For example, fullerenol-1 can be prepared from hydrolysis of the reaction products of fullerenes, either pure $C_{60}$ or a mixture of $C_{60}$ (84%) and $C_{70}$ (16%), with nitronium tetrafluoroborate in the presence of organocarboxylic acid ($RCO_2H$) at ambient temperature. Chiang, et al., U.S. Pat. No. 5,177,248; Chiang, et al. U.S. Pat. No. 5,294,732; and Chiang, et al., J. Am. Chem. Soc. 1992, 114, 10154; Chiang, et al., J. Am. Chem. Soc. 1993, 115, 5453. The structure of fullerenol-1 has been characterized to consist of $C_{60}O_x(OH)_y$ with x<5 and y=18 on average.

As another example, fullerenol-2 can be synthesized via hydrolysis of the reaction products of fullerenes, either pure $C_{60}$ or a mixture of $C_{60}$ (85%) and $C_{70}$ (16%), with a solution of sulfur trioxide (30%) in sulfuric acid. See Chiang, et al., J. Org. Chem. 1994, 59, 3960. The structure of fullerenol-2 has been characterized to consist of $C_{60}(OH)_y$ with y=12 on average.

Poly(sulfonylalkylated) fullerenes or their metal salts can be synthesized according to the method described in Example 1 below or methods analogous to it, followed by hydroxylation, if necessary. For example, once poly(sodium sulfonylbutylated) fullerene, $C_{60}(CH_2CH_2CH_2CH_2SO_3Na)_x$ where x, which varies with reaction conditions, ranges from 2 to 20 (on average 4–6), has been prepared (see Example 1, infra), it can then be hydroxylated by any of the methods described in the two preceding paragraphs to afford the corresponding mixed-functional fullerenes $C_{60}(CH_2CH_2CH_2CH_2SO_3Na)_x(OH)_y$ where y, which varies with reaction conditions, ranges from 1 to 20 (mostly 1–10).

Various well-established assays, such as those described in Examples 2–8, infra, can be used to screen for water-soluble fullerene compounds which are effective in treating free radical-related medical conditions.

As used herein, an effective amount of a fullerene compound described above is defined as the amount of the compound which, upon administration to a patient, reduces significantly the free radical level and improves the medical condition caused by the excessive amount of free radicals in the patient. The effective amount of a compound used to practice the present invention varies depending upon the medical disorder or disease to be treated, the manner of administration, the age, body weight, and other conditions of the subject of the subject to be treated, and ultimately will be decided by the attending physician. The effective amount of a compound to be administered to a patient is typically based on body surface area, patient weight, and patient condition. The interrelationship of dosages for animals and humans (based on milligrams per meter squared of body surface) is described by Freireich, E. J., et al., Cancer Chemother. Rep., 50(4), 219 (1966). Body surface area may be approximately determined from patient height and weight. See, e.g., Scientific Tables, Geigy Pharmaceuticals, Ardley, New York, pages 537–538, 1970. An effective amount of the compound for practicing the present invention can range from about 5 mg/kg to about 500 mg/kg, more preferably from about 5 mg/kg to about 250 mg/kg, and most preferably about 5 to about 150 mg/kg. Effective doses will also vary, as recognized by those skilled in the art, dependant on route of administration, excipient usage, and the possibility of co-usage with other therapeutic treatments.

The formulations may conveniently be presented in unit dosage form and may be prepared by any of the methods well known in the art of pharmacy. All methods include the step of bringing the active ingredient or ingredients into association with a suitable carrier which constitutes one or more accessory ingredients. In general, the formulations for tablets or powders are prepared by uniformly and intimately blending the active ingredient with finely divided solid carriers, and then, if necessary as in the case of tablets, forming the product into the desired shape and size. Of course, since the therapeutically active fullerene compounds described herein are water soluble, an aqueous carrier can be conveniently used.

The compound described above may be administered by any route appropriate to the condition being treated. Preferably, it is injected into the bloodstream of the subject being treated. However, it will be readily appreciated by those skilled in the art that the route, such as intravenous, subcutaneous, intramuscular, intraperitoneal, nasal, oral, etc., will vary with the condition being treated and the activity of the analog being used.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein, including patents, are hereby incorporated by reference in their entirety.

EXAMPLE 1

Synthesis of Water-Soluble Poly(sodium sulfonylbutylated) Fullerene Derivative $C_{60}$ $(CH_2CH_2CH_2CH_2SO_3Na)_x$ or Poly(sodium sulfonylpropylated) Fullerene Derivative $C_{60}$ $(CH_2CH_2CH_2SO_3Na)_x$ A round-bottom reaction flask A (100 ml) equipped with a magnetic stirrer was fitted with a septum and purged with $N_2$. It was charged with fullerene (500 mg), pure $C_{60}$ or fullerene mixtures, toluene (40 ml) and 1,4-butane sultone or 1,3-propane sultone (5–20 equiv. of fullerene). The solution was dried over molecular sieves (4 Å) prior to use. In a separated flask B, naphthalene (5–20 equiv. of fullerene) dissolved in dimethoxyethane (10 ml, dried over molecular sieves 4 Å prior to use) was allowed to react with sodium (5–20 equiv. of fullerene), forming a greenish complex solution of sodium naphthalide. This sodium naphthalide solution was then added into the reaction flask A via the syringe technique. The mixture was stirred at ambient temperature for 4 hours under $N_2$. At the end of reaction, it was added $H_2O$ (2 ml) to quench all reactive intermediates and the resulting solution was added into methanol (60 ml) to effect precipitation of brown solids. The solid precipitate was isolated by centrifugation. It was then washed twice with methanol (20 ml each time) and dried in vacuum at 40° C. to afford brown solids of water-soluble poly(sodium sulfonylbutylated), $C_{60}(CH_2CH_2CH_2CH_2SO_3Na)_x$, or poly (sodium sulfonylpropylated), $C_{61}(CH_2CH_2CH_2—SO_3Na)_x$, fullerene derivatives corresponding respectively to 1,4-butane sultone or 1,3-propane sultone used. The value of x varies with the amount of sodium naphthalide used in the reaction. Infrared data of poly(sodium sulfonylalkylated) fullerene derivatives are as follow: $IRv_{max}$ (KBr) 1642, 1570, 1384, 1192, 1038, 797, 750, 603 and 534 $cm^{-1}$.

EXAMPLE 2

Antioxidant Effect of Fullerenol-1

Under hypoxia conditions, such as hemorrhage and exsanguination-induced ischemia, the production of oxygen-derived radicals in airway tissues (Frank, J. Appl. Physiol., 1982, 53, 475; Prasad, et al. Angiology, 1988, 12, 1005) is expected to increase soon after the initiation of exsanguination. Both superoxide anion and hydrogen peroxide are produced by a metabolic pathway in vivo in the central nervous system (Halliwell, J. Neurochem., 1992, 59, 1609). The most reactive hydroxyl radicals can be generated subsequently by reactions of the iron complex with superoxide anion or hydrogen peroxide. Oxygen-derived radicals, especially hydroxyl radical, activate afferent C-fibers which, in turn, release tachykinins. The released tachykinins can cause noncholinergic airway constriction. Other than bronchoconstriction, reactive oxygen species also induce elevated mucus secretion and cause microvascular leakage leading to edema formation (Cees, et al. Free Radicals Biol. Med., 1990, 9, 381). The assays described below were conducted to test the efficacy of fullerenol-1 against exsanguination-induced noncholinergic airway constriction.

Acute adverse effect tests of fullerenol-1 on lung function of guinea pigs

Fullerenol-1 was used to explore whether it causes any acute adverse effects on lung function. Forty eight Hartley strain guinea pigs weighing 290±18 g were evenly and randomly divided into six groups: intravenous saline; intratracheal saline; intravenous fullerenol-1 (1); intratracheal fullerenol-1 (1); intravenous fullerenol-1 (2); and intratracheal fullerenol-1 (2). All animals were anesthetized with sodium pentobarbital (30–50 mg/kg). Each animal in the intravenous saline group was injected intravenously with 0.75 ml of saline solution while the same amount of saline was intratracheally instilled to each animal in the intratracheal saline group. 200 mg/kg of fullerenol-1 (in 0.75 ml solution) was administered intravenously or intratracheally to each animal in the fullerenol-1 (1) groups. Each animal in the fullerenol-1 (2) groups was intravenously or intratracheally administered with 2 mg/kg of fullerenol-1 (in 0.75 ml solution). Compared with the intravenous saline and intratracheal saline groups, the administration of fullerenol-1 did not cause significant alteration in respiratory function, indicating no adverse effect on bronchial function except administration via intratracheal instillation with high dosages (2 mg/kg).

Functional testing of antioxidant effect of fullerenol-1 on exsanquination-induced noncholinergic airway constriction 30 minutes after the administrations of saline or fullerenol-1 in a manner described above, pulmonary function tests were carried out. 30 two young male Hartley guinea pigs weighing 229±5 g were evenly divided into four groups: control; chronic hypoxia; fullerenol-1; and deferoxamine mesylate. Animals in the control group were placed in an opened hypobaric chamber with no subatmospheric pressure. Animals in the chronic hypoxia group were placed in the closed hypobaric chamber with a barometric pressure of 380 Torr for seven days. The animal were only exposed to hypoxia from 5 PM to 8 AM each day (intermittent exposure); the rest of the day they were exposed to room air. Each animal in the fullerenol-1 group was injected peritoneally with fullerenol-1 (10 mg/kg/day) for two days prior to the functional study. In addition, 2 mg/kg of fullerenol-1 was also injected intravenously 30 minutes prior to exsanguination. Each animal was anesthetized with pentobarbital sodium (30–35 mg/kg, ip) and cannulated with a tracheal tube. During artificial ventilation with a Harvard Rodent Respirator (Model 680), each guinea pig was placed supine inside a whole-body plethysmograph. The flow rate was monitored with a Validyne DP 45 differential pressure transducer as the pressure dropped across three layers of 325-mesh wire screen in the wall of the plethysmograph. Lung volume changes were obtained via integration of flow. Maximal expiratory flow-volume (MEFV) maneuvers were performed using the Buxco Pulmonary Maneuvers system (Sharon, Conn.). For the MEFV maneuver, the lung were inflated to total lung capacity (lung volume at airway opening pressure=30 $cmH_2O$) 4 times. At peak volume during the fourth inflation, the solenoid valve for inflation was shut off and immediately another solenoid valve for deflation was automatically turned on. The deflation valve was connected to a 20 L container, which maintained a substmospheric pressure of $-40$ $cMH_2O$. Meanwhile, the program picked the forced expiratory volume at 0.1 sec ($FEV_{0.1}$) from the volume-time tracing. Before and after each MEFV maneuver, functional residual capacity (FRC) was determined. Starting from FRC, the lungs were inflated with a standard neon (0.5%) gas mixture to 50% vital capacity. The equilibrated gas mixture was withdrawn and analyzed. The FRC was obtained by subtracting the instrumental dead space from the total volume. The animal were then exsanguinated by severing the abdominal aorta. Artificial ventilation was stopped and MEFV maneuvers were performed at 5, 10, 15, 20, 25, and 30 minutes after exsanguination. The $FEV_{0.1}$ was used as an indicator of bronchoconstriction (the change in airway dimension).

Antioxidant effect of fullerenol-1 on exsanguination-induced noncholinergic airway constriction determined by substance P levels The lung substance P, a tachykinin, was extracted from the isolated lung of guinea pigs, following the tests described immediately above by the method of Saria, et al. Am. Rev. Respir. Dis., 137, 1330 (1988). Substance P level was measured by enzyme immunoassay using a Substance P enzyme immunoassay kit obtained from Cayman Chemical Co. (Ann Arbor, Mich.). This assay is based on the competition between free substance P tracer (substance P linked to acetylcholinesterase) for a limited number of substance P-specific rabbit antiserum binding sites. The concentration of the substance P tracer was held constant while the concentration of free substance P standard varied. Thus, the amount of substance P tracer that was able to bind to the rabbit antiserum was inversely proportional to the concentration of free substance P in the well. This rabbit antiserum-substance P complex bonds to the mouse monoclonal rabbit antibody that had been previously attached to the well. The plate was washed to remove any unbound reagents, followed by the addition of Ellman's reagent (containing the substrate to acetylcholinesterase) was added to the well. The product of this enzymatic reaction had a distinct yellow color and absorbed strongly at 412 nm. The absorbance was inversely proportional to the amount of substance P in the sample.

Antioxidant effect of fullerenol-1 on exsanguination-induced noncholinergic airway constriction determined by neutral endopeptidase activity Tracheal neutral endopeptidase activity was determined using a modification of the methods of Orlowski, et al. Biochemistry, 20, 4942 (1981) and Haxhiu-Poskurica, et al. J. Appl. Physiol. 72, 1090 (1992). The frozen tracheas were thawed and minced into tubes containing 50 mM Tris, pH 7.4. The tissues were sonicated for 30 sec at 4° C. and centrifuged at 17,500 g for 15 minutes. The supernatant (tissue extract) was removed for analysis. The reaction mixture (250 ml) contained 50 ml of tissue extract, 1.25 mM glutaryl-alanine-alanine-phenylalanine-4-methoxy-2-naphthylamine substrate, 10 mg leucine aminopeptidase, and 50 mM Tris buffer, pH 7.4. The sample was incubated for 1 hour at 37° C. The product was colored by addition of fast garnet GBC (2 ml of 0.0025% solution) in Brij 35 (2%), giving optical absorptions at 530 nm. The amount of 2-naphthylamine released was calculated from the extinction coefficient. Each experiment was performed in duplicate. A 50 ml aliquot of each extract was also pre-incubated for 15 minutes at room temperature with $8\times10-7$ M phosphoramidon in 50 mM Tris buffer, pH 7.4. To this solution was added the substrate and leucine aminopeptidase and the mixture incubated at room temperature. The protein concentration of the trachea was determined with bovine serum albumin as the standard. The phosphoramidon-inhibitable neutral endopeptidase specific activity was expressed as nmoles of 2-naphthylamine released per mg protein per hour.

EXAMPLE 3

Inhibitory Effect of Fullerenol-1 on Hydrogen Peroxide-Induced Damages on Brain Tissues Male Wistar rats (100–140 g) were anaesthetized with ether and decapitated. The hippocampi were rapidly removed and placed in ice cold oxygenated (95% $O_2$ and 5% $CO_2$) artificial cerebrospinal fluid of the following composition (mM): NaCl 124, KCl 4.0, $KH_2PO_4$ 1.0, $MgCl_2.6H_2O$ 1.0, $CaCl_2$ 2.5, $NaHCO_3$ 26, and glucose 10.0. Slices with a thickness of 400 mm were cut from the mid-septotemporal regions of both hippocampi, perpendicular to the long axis of this structure, with a Sorval tissue chopper, followed by placing it in a recording chamber kept at 33–35° C. A gas mixture of $O_2$ (95%) and $CO_2$ (5%) was bubbled through the water bath surrounding the chamber, and the fluid level was maintained above the upper surface of the slice. The perfusion rate was kept at 6.0 ml/min. The slices were incubated for 1 hour prior to use.

Stimulation and recording paradigms in the hippocampal slice were performed using bipolar stimulating electrodes consisted of a 300 mm diameter Teflon-insulated stainless steel wire and an Ag—AgCl wire as the return path in the bath. Stimulation electrodes were placed, under visual guidance from a dissecting microscope, in stratum radiatum for orthodromic stimulation of Schaffer collateral pathway to the CA1 pyramidal cells. Stimulation conditions were 0.1 ms rectangular pulses of 5–15 V. Low frequency stimulation was elicited at a frequency of 0.2 Hz. Extracellular recording electrodes with tip layer of CA1 to record the somatic response. The amplitude of the population spikes was a function of stimulus intensity. Increasing the intensity of the stimulation also increased the amplitudes of the population spikes. A stimulation intensity which elicited half maximum of the amplitudes was used and kept constant throughout the experiment. For the paired pulse stimulation, the interval of 50 ms was used. Value of the paired pulse facilitation was obtained as the percentage difference in amplitude between the second and the first population spikes. The criterion for accepting a slice and starting a recording session was that maximal stimulation evoked a single population spike with an amplitude at least 5 mV. Stimulation voltages were adjusted to elicit baseline population spike amplitudes of half-maximum about 3 to 5 mV.

The amplitude of CA1 population spikes was recorded as 3.9±0.2 mV (n=13). This amplitude remained at the same level even after 200 minutes of incubation. Hydrogen peroxide decreased the amplitude of CA1 evoked population spikes in hippocampal slices in a concentration dependent manner. Hydrogen peroxide at concentrations higher than 0.006% decreased the amplitude of population spikes. Ten minutes after hydrogen peroxide (0.004%, 0.006%, 0.008% and 0.02%) administration, the amplitudes of the CA1 evoked population spikes were decreased to 98.0±1.0% (n=3), 32.3±4.9% (n=8), 15.2±2.8% (n=3), and 8.2±2.9% (n=3), respectively, of the pre-drug control level.

Fullerenol-1 (100 mM) itself has no detectable adverse effect on hippocampal slices, showing the amplitude of the CA1 evoked population spikes at 103.5±0.5% (n=5), 105.5±0.5% (n=3), and 106.5±1.5% (n=3) of the control amplitude after 5, 10, and 15 minutes of administration, respectively. A time-dependent sharp decline of population spike amplitude was observed with the administration of $H_2O_2$ (0.006%) alone to 32.3±4.9% (n=8) after a contact period of 10 minutes. Upon the administration of fullerenol-1 (100 mM) in a separated experiment, the population spike amplitude was found to be 103.0±0.5% (n=5) of the pre-drug control amplitude level. After the addition of $H_2O_2$ (0.006%) for a period of 10 minutes, the amplitude decreased to 74.6±5.5% (n=5). Replacement of the fullerenol-1 medium solution in the same experiment by a $H_2O_2$ solution resulted in a similar suppression behavior of $H_2O_2$ on nerve responses.

EXAMPLE 4

Inhibitory Effect of Fullerenol-1 on Cumene Hydroperoxide-Induced Damages on Brain Tissues A similar experimental preparation procedure as that described in Example 3 above was used. Cumene hydroperoxide decreased the amplitudes of CA1 evoked population spikes in hippocampal slices in a concentration dependent manner. 15 minutes after cumene hydroperoxide administration at a concentration of 0.5 and 1.0 mM, the amplitude of the CA1 evoked population spikes was found to decrease to 70.5±2.4% (n=3) and 34.5±5.4% (n=5), respectively, of the control amplitude level. If the hippocampal slice was incubated with fullerenol-1 (100 mM) for a period of 5 minutes prior to the addition of cumene hydroperoxide (1.0 mM), the population spike amplitude was found to be 102.8±1.9% (n=4) of the pre-drug control amplitude level. After the addition of cumene hydroperoxide (1.0 mM) for a period of 15 minutes, the amplitude decreased to 75.6±3.1% (n=4), which is roughly 2.1 times higher in intensity than that of spike without fullerenol-1.

EXAMPLE 5

Effect of Fullerenol-1 in Preserving Ischemia-Reperfusion Related Injuries

A canine auto-transplantation model was used for the evaluation of free radical scavenging efficiency of fullerenol-1 in preserving ischemia-reperfusion related injuries. After anesthesia were induced in mongrel dogs (n=8–10 for each group), bilateral nephrectomies were done through midline transperitoneal incision. The harvested kidneys were flushed with 4° C. perfusate after certain period of warm ischemia. After 24 hours of simple hypothermic storage, the kidneys were implanted into the subcutaneous cervical pouches of the same dog through a midline cervical incision with the renal artery anastomosed to the common carotid artery and the renal vein to the external jugular vein, both in the end to end fashion. Blood and urine samples were collected before harvest and 1 hour after auto-transplantation, each for two consecutive 30-minute periods. The dependent variables included the presence or absence of fullerenol-1 (20 mM) in the Euro-Collin perfusate and the duration of warm ischemia (3 minutes vs. 30 minutes). Assessment of the renal function was performed by comparison of the pre-harvest and early post-transplantation biochemical parameters, which consisted of serum blood urine nitrogen or BUN, serum creatinine, creatinine clearance (CCr), urine flow rate, fractional reabsorption or excretion of urinary sodium and potassium ions. High performance liquid chromatographic analyses for adenonucleotides concentrations of the biopsied kidney tissues before harvest, before and after revasculization, as well as histopathological observations for each representative specimen, were also performed.

In each arm, the post-autotransplant data showed deteriorated renal functions as compared with those of the pre-harvest ones. The pre-harvest biochemical data were similar in each group. When the post-autotransplant results were compared in both the 3- and 30-minute ischemic groups, the respective CCr data of 4.5±1.6 and 2.8±0.5 ml/min and the respective total sodium reabsorption amount of 456±213 and 218±56 mmol/min, with the application of fullerenol-1 (20 $\mu$M) in the perfusate, were significantly improved, as compared with the data obtained from the control experiment (without fullerenol-1): 6.2±2.3 and 5.1±1.5 ml/min, respectively, for CCr and 663±308 and 459±183 mmol/min, respectively, for total sodium reabsorption. Histopathological sections of the biopsied kidney specimen were performed with H & E stain and examined under light microscopy. When the post-reperfusion slides were compared, the kidney tissues in experiments applying fullerenol-1 (20 mM) in the perfusate solution showed a less degree of inflammatory cells infiltration, less tubular swelling and necrosis, and less patchy hemorrhage. The differences were more prominent in the 30-minutes warm ischemia group.

Analyses of the adenonucleotide concentrations in the biopsied kidney tissues revealed that high energy substance (ATP) concentration was decreased after the ischemic process and trends return to the pre-harvest baseline level after revasculization. When the ATP concentrations in the various post-autotransplant tissues were compared, the concentration in experiments applying fullerenol-1 (20 mM) in the perfusate solution was higher than that of the control.

EXAMPLE 6

Inhibition by Poly(sodiumsulfonylbutylated) Fullerene of Lipid and Lipoprotein Peroxidation Water-soluble poly(sodiumsulfonylbutylated) fullerene was used in the study of its inhibitive effect on lipid and lipoprotein peroxidation, a major contributing factor in the pathogenesis of atherosclerosis.

VLDL (<1.01 g/ml), LDL (1.02–1.06 g/ml), HDL2 (1.06–1,12 g/ml) and HDL3 were isolated from the plasma of normal human subjects after overnight fasting and collected with EDTA (1 mg/ml) by sequential ultracentrifugation in sodium bromide solution. Freshly isolated lipoproteins were stored at 4° C. under $N_2$ and used within one week. Their protein contents were measured by the Lowry method, using bovine serum albumin as the standard. For oxidation experiments, lipoproteins were dialyzed in a phosphate buffer saline (PBS, 0.01 M) and NaCl (0.15 M) solution (pH 7.4) at 4° C. for 24 hours. All dialyzed VLDL (20 mg/ml), LDL (100 mg/ml), HDL2 (100 mg/ml) and HDL3 (100 mg/ml) were peroxidized in PBS at 37° C. under different oxidative conditions induced by each of the following reagents: $Cu^{+2}$ (2.0 mM), 2,2-azobis(2-amidinopropane) hydrochloride (AAPH, 1.0 mM), 2,2-azobis(2,4-dimethyl-valeronitrile) (AMVN, 1.0 mM), and xanthine (80 mM)/xanthine oxidase (0.01 U). The progress of peroxidative incubation was systematically followed via spectroscopic methods and terminated by the addition of EDTA (3 mM) and antioxidant butylated hydroxytoluene or BHT (100 mM) under cooling when a steady state of the maximum lipoprotein peroxidative modification was reached. The degree of lipoprotein oxidation was detected with or without the application of water-soluble poly (sodiumsulfonylbutylated) fullerene (10–500 mM). Addition of this fullerene derivative was made either prior to the reaction or at the early stage of the propagation phase of oxidation reactions.

Kinetics of conjugated dienes formation was followed by continuously monitoring the change of optical absorbance at 234 nm vs. time. Duration of the lag time was calculated by extrapolating the slope of the sharp-rising optical absorption curve, corresponding to the propagating phase of the reaction. The thiobarbituric acid reactive substances contents (TBARS) were used to correlate the lipid peroxidation level, as malondialdehyde equivalents. The reaction was carried out by incubating native or oxidized lipoproteins with thiobarbituric acid at 95° C. for 1 hour. After cooling the mixture to room temperature, resulting adducts were extracted by n-butanol. The n-butanol extract was subjected to the florescence measurements using an excitation irradiation with a wavelength of 515 nm and detecting the emitted florescence at 552 nm.

Incubation of freshly isolated human lipoprotein in PBS with AAPH or AMVN at 37° C. for 24 hours resulted in extensive, oxidative modification of lipoprotein. Simultaneous addition of the sulfonylbutylated fullerene inhibited the lipoprotein oxidation in a concentration dependent manner. Nearly complete inhibition (>90% for most cases), giving a minimum amount of detectable TBARS products, was observed when a 500 mM concentration of sulfonyl-butylated fullerene was applied in all cases. Divalent $Cu^{+2}$ ion induced a significant level of oxidation on all lipoproteins. In the case of HDL oxidation induced by $Cu^{+2}$, sulfonylbutylated fullerene were able to provide an inhibition efficiency of larger than 80% with a concentration of 20 mM. The lag and peak times in kinetic oxidation measurements of $Cu^{+2}$-induced formation of conjugated dienes in lipoproteins were shown to increase significantly with a decreased propagation rate upon the addition of sulfonylbutylated fullerene at a concentration of as low as 10 mM. The high inhibitory effect of the sulfonylbutylated fullerene on lipoprotein oxidation was observed not only during the initial phase, but also in the oxidation propagation phase.

EXAMPLE 7

Antiproliferative Effect of Fullerenol-1 and -2 on Human T-Lymphoid Leukemia CEM Cells The antiproliferative effect of fullerenol-1 and fullerenol-2 was measured as their ability to inhibit the proliferation of cultured human T-lymphoid leukemia CEM cells induced by the fetal calf serum. Assessment of the effect of fullerenol-1 and fullerenol-2 on the tumor cell proliferation was performed by assay of [$^3$H]thymidine incorporation during the synthesis of DNA in proliferative cells (see Watabe, et al., J. Natl. Cancer Inst. 1984, 72, 1365). The human T-lymphoid leukemia cells CEM (the American Type Culture Collection, Rockville, Md.) was cultured in RPMI-1640 medium containing 10% fetal calf serum. Cell viability was determined with the trypan blue dye exclusion method. Experiments were carried out by the addition of fullerenol-1 or fullerenol-2 into the suspension of tumor cells ($5\times10^3$ cells/well). The control wells were incubated with the suspension of tumor cells in the absence of fullerenols. All reactions were incubated in a $CO_2$ incubator at 37° C. for 0.5 hours prior to the addition of [$^3$H]thymidine (1 mCi) to each well. After an additional 4 hours of incubation, cells were harvested and the amount of [$^3$H]thymidine incorporated into cells was counted.

The control value for incorporation of [$^3$H]thymidine in proliferative cultures of human T-lymphoid leukemia cells (CEM cells, $5\times10^3$ cells/well), induced by 10% fetal calf serum, was found to be 7,031±322 cpm/well. Upon exposure of human T-lymphoid leukemia cells to fullerenols, in a dose concentration of $10^{-6}$ to $10^{-4}$ M, the incorporation of [$^3$H]thymidine in the final cell products was largely inhibited. A sharp decrease of proliferative response was observed as the dose concentration increased. The $IC_{50}$ values (n=5) for fullerenol-1 and fullerenol-2 were determined to be 17.8±4.0 and 28.2±4.0 mM. The maximal inhibitory activities of water-soluble fullerenol-1 and fullerenol-2 at a dose level of 10–4 M were found to be 72.0±5.0 and 68.5±5.0 %, respectively. Comparison of these data with the inhibitory activities of ascorbic acid (vitamin C) showed that it requires more than 30 times as much ascorbic acid as fullerenol-1 to achieve 50% inhibition of the proliferative activities. These results demonstrated that water-soluble fullerenols exhibited the antiproliferative effects on cancer cells such as human T-lymphoid leukemia cells.

EXAMPLE 8

Antiproliferative Effect of Fullerenol-1 and -2 on Smooth Muscle Cells

The presence and growth of smooth muscle cells as an entangled structure with connective tissues and lipids in both fatty streaks and fibrous plaques is a critical factor in determining the progress of atherogenesis (Ross, New Engl. J. Med., 1986, 314, 488).

The antiproliferative effect of fullerenol-1 and fullerenol-2 was measured as their ability to inhibit the proliferation of cultured rabbit aortic smooth muscle cells induced by the fetal calf serum (Huang, et al. Eur. J. Pharmacol., 1992, 221, 381). Specifically, the intima and inner two-thirds of the cell-containing media were removed from the isolated rabbit aorta in strips of 1 mm in width. The strips were cut into square pieces and placed in a dry petri dish. The dish was then filled with the DMEM medium supplemented with 10% fetal calf serum. When the cells approached confluence in medium, the aorta pieces were removed. Cells between passages 3 and 8 were used. Cell viability was determined with the trypan blue dye exclusion method.

The proliferative response of vascular smooth muscle cells was determined via the uptake of tritiated thymidine during the synthesis of DNA in proliferative cells. Prior to all experiments, confluent smooth muscle cells ($2.5 \times 10^4$ cells/well) were rendered quiescent by culturing for 48 h in 0.5% fetal calf serum. The medium was then charged with stimulator, 5% fetal calf serum, and fullerenols. The resulting mixture was kept for 24 hours before the subsequent addition of [$^3$H]thymidine (0.2 mCi/well). After an additional twenty-four hours of culturing, the cells were harvested and the incorporated [$^3$H]thymidine in the DNA structure of proliferated cells was counted by a liquid scintillation counter. Each experiment was performed in triplicate. The inhibitory activities of fullerenols were expressed as percentages of the untreated control value, incurred in response to the addition of stimulator under similar conditions in the absence of fullerenols. The concentration evoking 50 percent of the maximal inhibition ($IC_{50}$) was calculated accordingly for each experiment. The control value for the incorporation of [$^3$H]thymidine in proliferative cultures of rabbit vascular smooth muscle cell, induced by 5% fetal calf serum, was found to be 12,527±2,011 cpm/well. Exposure of smooth muscle cells to fullerenols, in a dose range of $10^{-7}$ to $10^{-4}$ M, inhibited significantly the incorporation of [$^3$H]thymidine in the final cell products. That resulted in a sharp decrease of proliferative response as the dose concentration increases. The $IC_{50}$ values (n=7) were determined to be 0.48±0.15 and 2.0±0.5 mM for fullerenol-1 and fullerenol-2, respectively. The maximal inhibitory activities of water-soluble fullerenol-1 and fullerenol-2 at a dose level of $10^{-4}$ M were found to be 98.0±1.7 and 86.0±9.8%, respectively. Comparison of these data with the inhibitory activities of ascorbic acid (vitamin C) showed that it requires more than 440 times as much ascorbic acid as fullerenol-1 to achieve 50% inhibition of the proliferative activities. These results demonstrated that water-soluble fullerenols possess antiproliferative activities on rabbit vascular smooth muscle cells and therefore are useful in the treatment of proliferative disorders of smooth muscle cell, such as atherosclerosis and restenosis.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating a free radical-related medical condition, said method comprising administering to a subject in need thereof an effective amount of a compound of the formula $$F(-X)_m$$

wherein

F is a fullerene core;

each X is independently OH, $(CH_2)_n-SO_3H$, or a metal salt of $(CH_2)_n-SO_3^-$ in which each n is independently 2–50; and m is 2–40.

2. The method of claim 1, wherein X is OH.

3. The method of claim 2, wherein m is 4–30.

4. The method of claim 3, wherein m is 10–20.

5. The method of claim 4, wherein said fullerene core is a $C_{60}$ fullerene core.

6. The method of claim 1, wherein X is $(CH_2)_n-SO_3H$ or a metal salt of $(CH_2)_n-SO_3^-$.

7. The method of claim 6, wherein m is 2–10.

8. The method of claim 7, wherein n is 2–10.

9. The method of claim 8, wherein said fullerene core is a $C_{60}$ fullerene core.

10. The method of claim 6, wherein n is 2–10.

11. A pharmaceutical composition for treating a free radical-related medical condition, said composition comprising an effective amount of a compound of the formula $$F-(X)_m$$

wherein

F is a fullerene core; each X is independently $(CH_2)_n-SO_3H$ or a metal salt of $(CH_2)_n-SO_3^-$ in which each n is independently 2–50; and m is 2–40; and a pharmaceutically acceptable carrier thereof.

12. The pharmaceutical composition of claim 11, wherein m is 2–10.

13. The pharmaceutical composition of claim 12, wherein n is 2–10.

14. The pharmaceutical composition of claim 13, wherein said fullerene core is a $C_{60}$ fullerene core.

15. The pharmaceutical composition of claim 11, wherein n is 2–10.

* * * * *